(12) United States Patent
Lisec

(10) Patent No.: US 7,526,968 B2
(45) Date of Patent: May 5, 2009

(54) DEVICE FOR PIPETTING A LIQUID

(75) Inventor: Thomas Lisec, Itzehoe (DE)

(73) Assignee: Fraunhofer-Gesellschaft zur Förderung der Angwandten Forschung E.V., Munich (DE)

( * ) Notice: Subject to any disclaimer, the term of this patent is extended or adjusted under 35 U.S.C. 154(b) by 364 days.

(21) Appl. No.: 10/484,740

(22) PCT Filed: Jul. 24, 2002

(86) PCT No.: PCT/EP02/08248

§ 371 (c)(1),
(2), (4) Date: Jul. 17, 2006

(87) PCT Pub. No.: WO03/011462

PCT Pub. Date: Feb. 13, 2003

(65) Prior Publication Data

US 2008/0184822 A1    Aug. 7, 2008

(30) Foreign Application Priority Data

Jul. 24, 2001    (DE) ................ 101 35 963

(51) Int. Cl.
*B01L 3/02*    (2006.01)
(52) U.S. Cl. ................ 73/864.14; 73/863.32
(58) Field of Classification Search ........... 73/864.14, 73/863.32
See application file for complete search history.

(56) References Cited

U.S. PATENT DOCUMENTS

| | | | | |
|---|---|---|---|---|
| 3,430,628 A * | 3/1969 | Wiggins | ................ | 73/863.32 |
| 4,748,859 A * | 6/1988 | Magnussen et al. | ... | 73/864.14 X |
| 4,961,350 A * | 10/1990 | Tennstedt | ............ | 73/864.14 X |
| 5,193,403 A | 3/1993 | Burgisser | ................ | 73/864.17 |
| 5,312,757 A * | 5/1994 | Matsuyama et al. | ........... | 436/54 |
| 5,497,670 A * | 3/1996 | Carl | ................ | 73/863.32 |
| 5,827,745 A * | 10/1998 | Astle | ................ | 73/863.32 X |
| 6,199,435 B1 * | 3/2001 | Wilmer et al. | ........... | 73/864.14 |
| 6,748,804 B1 * | 6/2004 | Lisec et al. | ............... | 73/304 R |
| 6,780,381 B2 * | 8/2004 | Yiu | ................ | 73/864.14 X |
| 6,955,077 B2 * | 10/2005 | Blaszcak et al. | ............... | 73/73 |
| 6,997,066 B2 * | 2/2006 | DeSilva et al. | ........... | 73/863.31 |

(Continued)

FOREIGN PATENT DOCUMENTS

DE    3839896    6/1989    ............... 422/100

(Continued)

OTHER PUBLICATIONS

JP 09127129 A, May 1997, Japan, Takagi, Yasumitsu, its Derwent Abstract.*

*Primary Examiner*—Thomas P Noland
(74) *Attorney, Agent, or Firm*—Antonelli, Terry, Stout & Kraus, LLP.

(57) ABSTRACT

A device is disclosed for pipetting a liquid, comprising a pipette body enclosing a pipette volume, into which a fluid medium can be placed and in which an actuator that controllably displaces the medium in the pipette volume is provided, as well as a pipette tip, which can be connected to the pipette volume in a fluid-tight manner. The present invention is distinguished by the pipette volume and the pipette tip being connected via a fluid-tight connecting means directly or indirectly to each other in such a manner that the pipette tip is moveable relative to the pipette volume.

23 Claims, 3 Drawing Sheets

U.S. PATENT DOCUMENTS

2003/0143316 A1* 7/2003 Eipel et al. .................. 427/2.11
2006/0034732 A1* 2/2006 Bargh et al. .................. 422/100

FOREIGN PATENT DOCUMENTS

| | | |
|---|---|---|
| DE | 4214430 | 6/1994 |
| DE | 4416406 | 12/1995 |
| DE | 19845950 | 3/2000 |
| DE | 19944331 | 4/2001 |
| DE | 10017105 | 10/2001 |
| EP | 215536 A2 * | 3/1987 ............. 73/863.32 |
| GB | 2249171 | 4/1992 |
| WO | 9832000 | 7/1998 |
| WO | WO 0136933 A1 * | 5/2001 |

* cited by examiner ( State of the Art )   Fig. 2

( State of the Art )

DEVICE FOR PIPETTING A LIQUID

BACKGROUND OF THE INVENTION

1. Technical Field

The present invention relates to a device for pipetting a liquid, comprising a pipette body enclosing a pipette volume in which a fluid medium can be placed and in which an actuator that controllably displaces the medium in the pipette volume is provided, as well as a pipette tip that can be connected in a fluid-tight manner to the pipette volume.

2. Description of the Art

For example, in studying the findings of diagnostic examinations or routine physical examinations, modern medicine is increasingly relying on quantitative analysis of relevant substances in body fluids. The number of to-be-examined substances is continuously growing as is test frequency. Increasing numbers of analyses with simultaneously decreasing costs requires, in particular, lowering the need for reactants, which are often quite expensive. Therefore, the trend in development is to focus on precise dosage of as small as possible amounts of liquid.

Used for this purpose is high-throughput screening, which permits studying the interaction of a drug, molecule or a cell with a great number of different substances in an economical manner. Defined volumes of corresponding solutions are brought to react in microtiter plates, in short MTP. In order to be able to work quickly and cost-effectively, the testing volumes are further miniaturized. In a 1536 microtiter plate, the volumes, after addition of all substances and reactants are less than 10 µl.

As the mixture ratio of the to-be-tested substances and the reactants may vary considerably, amounts of liquid in the µl range must be dosed precisely. Moreover, in order to avoid contamination effects, it is essential, in particular, that the smallest amounts are the first to be dispensed into the individual, separate dry reaction chambers, the so-called wells, on the microtiter plate.

If one and the same volume of the same liquid is to be distributed into a multiplicity of wells, piezoelectric (also see "nano-plotter" at http://www.qesim.de or "Genesis NPS" at http://www.tecan.de) or ink jet microdispenser systems (see D. Rose, "Microdispensing Technologies in Drug Discovery", DDT, vol. 4, No. 9, 1999) can be utilized very effectively, which are able to "shoot" tiniest drops into the individual wells without coming into contact.

FIG. 2, shows a known drop dispensing system based on a state-of-the-art piezoelectric pump. The dispensing system comprises a microtiter plate MTP disposed on a housing G, over which a needle pipette N with a single pipette channel is provided in a three-dimensionally turnable manner. Provided in the housing G is an injection pump S which conveys a carrier fluid T to the needle pipette N via a fluid-filled tube L. The needle pipette N is provided with a piezo-pump PP through which the carrier fluid T can be made to start oscillating in the needle pipette N. An air bubble B separates a liquid sample P from the carrier fluid T in the pipette tip PS. In this manner, excited by pressure oscillations in the carrier fluid, tiniest drops of the sample liquid are shot into the individual wells W on the microtiter plate MTP.

A drawback is that due to functional determinations, a relatively large minimal sample volume of several µl has to be accommodated in the pipette tip. If a very small amount of sample liquid is to be dispensed only once, a major part of the, in some cases very expensive, sample material is wasted. Furthermore, dosing viscous liquids in this manner is difficult. Moreover, piezo-pumps are very expensive and have hitherto been built with only 8 parallel pumps. Also known are Cartesian Technologies' pipette arrangements with 96 pipettes, which, however, are extremely complex as each pipette channel requires a tip. The aforementioned methods are very vulnerable to disturbances as the dosage process can only be controlled to a limited extent.

If, however, a multiplicity of different samples need to be dispensed only once, for example, a MTP copied or converted, pipette devices according to the so-called displacement principle are still employed, which are provided with 96 or 384 parallel channels. FIGS. 3a and 3b each show a piston-driven pipette array. In FIG. 3a, only a single large piston K serves as the drive for the entire pipette array PA, e.g. in CyBio AG's devices, see "Cybi-Well 2000" at http://www-.cybio-ag.com. The samples are sucked on or dispensed via an air cushion. As disposable plastic tips PS can be used, the risk of contamination by entrainment of sample remains is very small. Due to the elasticity of the relatively large air cushion, the minimal pipette volume is limited to approximately 1 µl. In FIG. 3b, every single pipette channel PK is provided with a separate piston, which is moved by a common drive A, for example as in Robbins Ltd.'s "Hydra", at http://www.robsci-.com. As, in this case, the samples can be manipulated almost without an air cushion, sub-µl volumes can be conveyed. However, instead of replaceable plastic tips PS, special, firmly held steel needles are employed, which require complicated rinsing following each pipetting procedure.

As none of the prior art pipetting systems permit checking how much sample liquid has actually been dispensed into each single well, it must always be ensured that the change in volume due to the piston movement is conveyed evenly and accurately into the pipette tips. Therefore, in all the prior art pipetting devices working in an array, the pipette tips are rigidly attached to the pipette head in which the piston is provided. Reusable tips are screwed fast onto the pipette head. On the other hand, disposable plastic tips are immobilely stuck into or clamped onto a receiving plate with corresponding connecting pieces.

In order to be able to guarantee that the desired amount of sample liquid is conveyed from each single pipette tip into the corresponding well, it must furthermore be ensured that the pipette tip or at least the amount of separated liquid conveyed from the pipette tip comes into contact with the surface of the well, if a method of drop discharge, as mentioned in the introduction hereto with reference to FIG. 2 is to be obviated. Fundamentally, precise operating X-Y-Z positioning devices for micropipette units relative to MTPs are known but problems crop up when the MTP curves or buckles three-dimensionally. Thus, under circumstances, not all the pipette tips of an array or the separated amounts of sample come into contact with the bottoms of the wells. Consequently, in some cases, no sample liquid is conveyed onto the MPT, but rather the sample remains hanging on the tip. Errors of this type occur spontaneously and can only be detected by visual control of the finished, pipetted MTP.

Robbins Ltd. (http://www.robsci.com) has discovered a special solution for avoiding the aforedescribed problem. The long, thin steel pipette needles set down on the bottom of the MTP with a thrust in such a manner that they bend with little elasticity. In this manner, it is ensured that all the tips really do come into contact with the bottom of the wells. If, on the other hand, disposable plastic tips are to be employed for pipetting, this method does not work, because the standard plastic tips are very rigid. If corresponding pressure were exerted on them, they would deform irreversibly but not bend.

SUMMARY OF THE INVENTION

In particular with regard to the manner of examining a multiplicity of substances by means of high-throughput screening described in the introduction, the invention is intended to ensure that the conveyance of liquid from each single pipette tip into the well allocated to it on a microtiter plate occurs reliably even if a microtiter plate should be uneven. In particular, the invention is a device for pipetting a liquid, comprising a pipette body enclosing a pipette volume, in which a fluid medium can be placed and in which an actuator that controllably displaces the liquid in the pipette volume is provided, as well as a pipette tip, which can be connected fluid-tight to the pipette volume, in such a manner that using simple constructive and cost-effective means, it is ensured that the pipette tip makes contact in a manner as required for conveying the liquid from the pipette tip onto the bottom of the well. Such a type device, which initially relates to a single pipette, should in particular be applicable in the same manner to an array-like arrangement of a multiplicity of pipettes. Thus, the invention provides a corresponding pipette array.

In particular, disposable pipette tips are connected to the corresponding pipette body in a replaceable manner.

An element of the invention is a device for pipetting a liquid, comprising a pipette body enclosing a pipette volume, in which a fluid medium can be placed and in which an actuator which controllably displaces the medium in the pipette volume is provided, as well as a pipette tip, which can be connected fluid-tight to the pipette volume, in such a manner that the pipette volume and the pipette tip are connected directly or indirectly via a fluid-tight connecting means so that the pipette tip is moveable relative to the pipette volume.

The present invention is based on mechanical decoupling between the pipette tip and the pipette body in such a manner that the pipette tip can be moved practically freely but preferably can be moved along a linear axis.

BRIEF DESCRIPTION OF THE DRAWINGS

The present invention is described, by way of example without the intention of limiting the overall inventive idea, using embodiments with reference to the accompanying drawing.

FIG. 2 shows a representation of a state-of-the-art drop-dispensing system, FIGS. 3a and b show a representation of a state-of-the-art piston-driven pipette array.

DETAILED DESCRIPTION OF THE INVENTION

Figure 1:
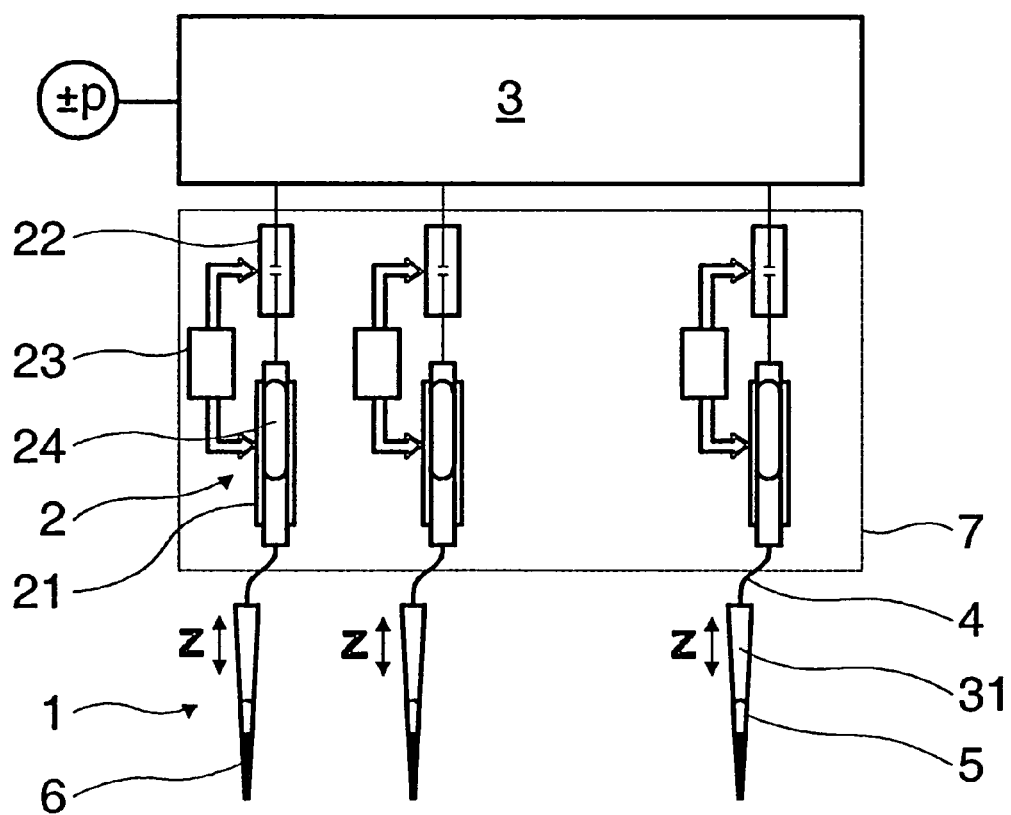
FIG. 1 shows a preferred embodiment of a pipette system having a multiplicity of single pipettes.
Figure 3A:
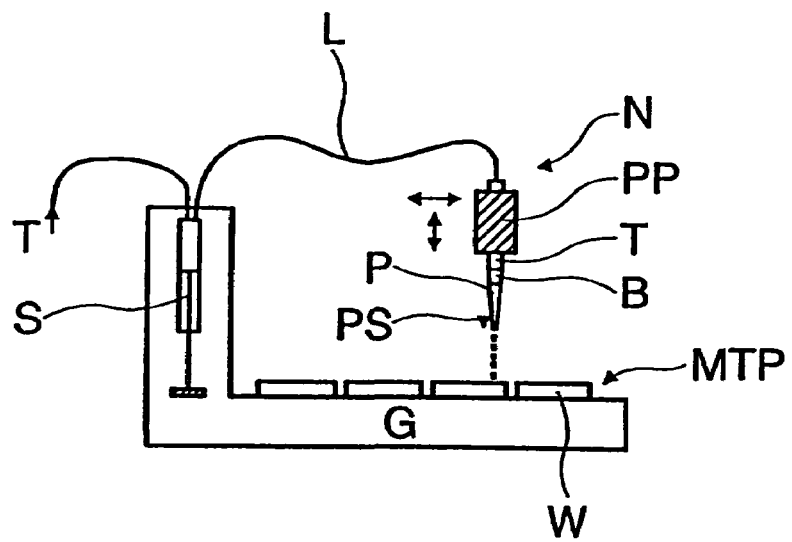
Figure 3B:
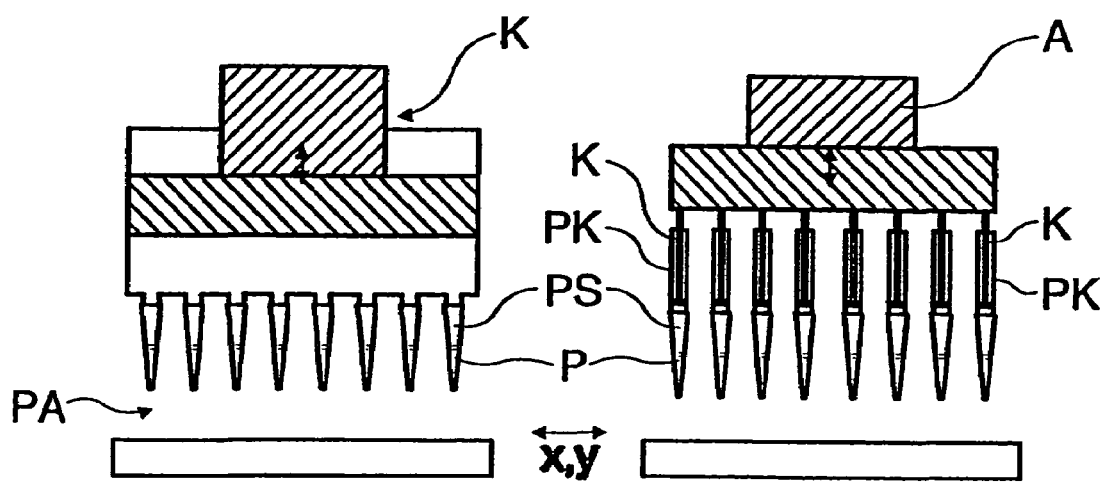

FIG. 1 shows a schematic representation of a pipette system provided with a multiplicity of linearly or array-like disposed pipette tips 1, a corresponding multiplicity of pipette bodies 2 allocated to each single pipette tip 1 and a reservoir volume 3 for supplying a fluid medium in the form of a system fluid.

In the depicted embodiment each single pipette body comprises a pipette volume 21. The pipette body 2 is connected to an actuator 22, which in the form of a valve conveys the system fluid 31 into the pipette volume 21 in doses. Moreover, the pipette body 2 provides a depletion level sensor 23, which is described in particular in DE 199 44 331 A1. The depletion level sensor 23 is composed of a detector system, which detects the phase limit in the pipette volume between the system fluid 31 and an air bubble 24 enclosed in the pipette volume. With the aid of a monitoring electronics designed as an ASIC, which will not be explained in more detail but rather relating thereto see the aforementioned DE 199 44 331 A1, an actuator 22 designed as a valve is activated in dependence on the detected current depletion level in the pipette volume. The air bubble 24 enclosed in the pipette volume 21 is surrounded from both sides by the system fluid 31.

Each single pipette tip is connected to the pipette volume 21 via a flexibly designed, fluid-tight connecting means 4, which preferably is designed as a flexible tube, which itself only possesses little or preferably no expandability in order to be able to rule out changes in volume in the tube due to high pressure building up therein. The system fluid 31 reaches in this manner via tube 4 into the pipette tip, in which it in turn is separated on one side by an air bubble 5. The air bubble 5 in turn separates an amount of sample liquid 6, which is to be conveyed into a dry well by the pipette procedure.

As the forces and the pressures required to move the air bubble 24 and thus also the system fluid 31 in the pipette volume 21 are very low, the pipette tips 1 can each be coupled without further precautions to the flexible piece of tube 4. In this manner, they are not fixedly connected to the pipette body 2 and can be moved depending on the length of the connecting tube 4 relative to the pipette body, for example in the mm range without significantly impairing pipetting precision, for example due to deformation of the connecting tube. Therefore, in selecting the material of the connecting tube 4, care must be taken that tube materials are employed which possess negligible volume deformation properties during corresponding bending of the tube. By means of corresponding activation of the actuator, the air bubble 5 is moved by the system fluid in direction of the pipette tip opening due to which the sample liquid 6 is displaced out of the pipette tip. The displacement process is exactly controlled due to the depletion level sensor. In this manner, it can be prevented that system fluid is also conveyed out of the pipette tip opening.

The pipette bodies 2 of all the linearly respectively array-like disposed pipettes in FIG. 1 are borne together in a component 7 (see broken-line boundary).

Figure 4A:
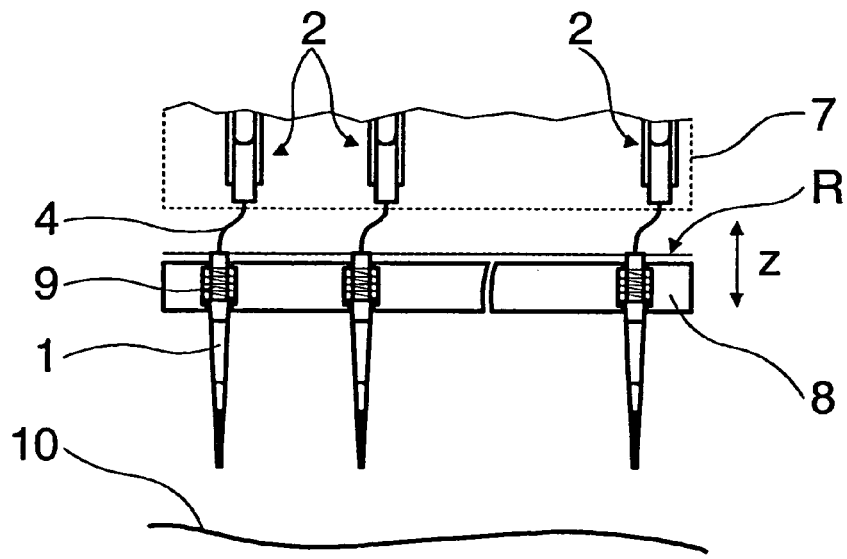
FIGS. 4a and b show sequential representations for lowering array-like disposed pipette tips onto an uneven work surface.
Figure 4B:
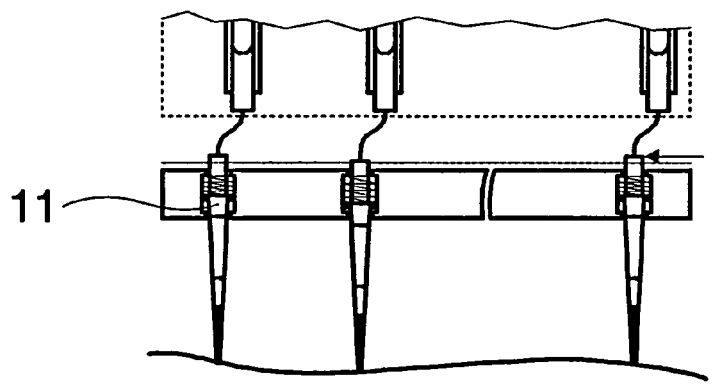
Figure 4C:
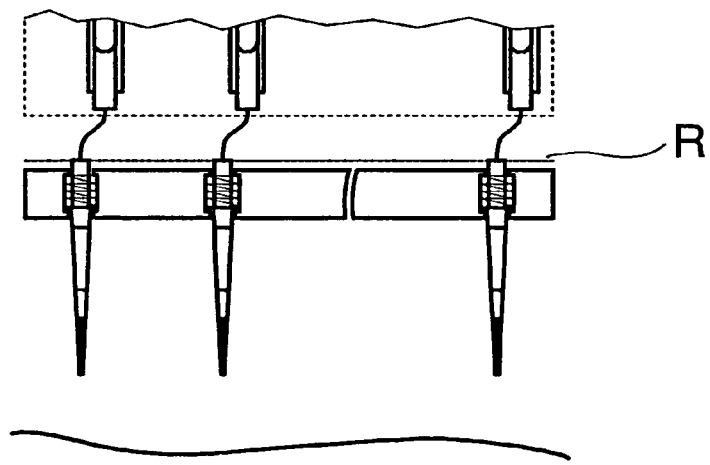

An advantageous embodiment also provides for the common bearing of all the pipette tips 1, as shown in FIGS. 4a-c.

In FIGS. 4 a-c, the individual pipette tips 1 are depicted borne in a spring-resilient manner in a uniform holding unit 8. The space between the holding unit 8 and the component 7, in which the single pipette bodies 2 are disposed is defined and amounts to maximally the length of a single connecting tube 4. Each single pipette tip 1 is borne under spring tension in the z-direction and can be moved upward in the z-direction when coming into contact with the bottom of the well to dispense sample liquid. The spring effect, with which each single pipette tip 1 is borne in the holding unit 8, can also come from the inherent elasticity of the connecting tube 4 or, as shown in the preferred embodiment according to FIG. 4, from a spring element 9 provided for each pipette tip 1 in the holding unit 8.

However, the spring-resilient manner of bearing can fundamentally also be realized for each individual pipette tip 1, as depicted, but also collectively, depending on the pipetting process, for groups of pipette tips.

In the sequential representation according to FIG. 4a, the pipette arrangement is located without coming into contact with above an uneven surface 10. The individual pipette tips 1 are in an idle position R due to the spring-tensioned bearing (for this see dotted line).

In FIG. 4b, the individual pipette tips 1 are pressed against the work surface 10 to dispense the sample in such a manner that the individual pipette tips 1 move forward against the spring force of each individual spring element 9 relative to the idle position R in the z-direction. Depending on the depth of lowering of each individual pipette tip 1, the forward movement in the z-direction is of different length for each pipette 1 (see arrow).

In FIG. 4c, the pipette process has been completed and the pipette arrangement has been lifted from the work surface 10 and the pipette tips have returned to their idle position R.

Due to the manner of bearing each single pipette tip, it is achieved that all the pipette tips of the pipette array always come into contact with the bottom of the wells of a microplate even if the microplate is executed uneven.

Fundamentally, the pipette tips 1 can be implemented as one-piece and integrated in the holding unit 8 for multiple repetition of the pipetting procedure. This, however, requires thorough cleaning of the pipette tips between two successive pipetting procedures.

Furthermore, the device also permits using disposable pipette tips, obviating the washing procedure after completed pipetting. For this purpose, holding device 8 provides intermediate pieces 11, which are integrated in the holding unit 8 by means of corresponding bearing, for example with the aid of the spring element 9. A respective tip designed as a disposable pipette tip can be clamped or screwed onto the respective intermediate piece 11 by means of corresponding connecting pieces.

LIST OF REFERENCE NUMBERS 1 pipette tip
2 pipette body
21 pipette volume
22 actuator
23 depletion level sensor
24 air bubble
3 reservoir volume
31 rinsing liquid (fluid medium)
4 flexible, fluid-tight connecting means
5 air bubble
6 sample liquid
7 component
8 holding unit
9 spring element
10 work surface
11 intermediate piece

What is claimed is:

1. A device for pipetting a liquid, comprising a pipette body, enclosing a pipette volume, for contacting a fluid medium, an actuator for controllably displacing the fluid medium in the pipette volume, a pipette tip, which is connectable to the pipette volume in a fluid-tight manner and movable relative thereto, and a holding unit bearing the pipette tip, the pipette tip being axially movable in the holding unit; and wherein the pipette volume and the pipette tip are connected by a fluid-tight flexible tube directly or indirectly to each other, the fluid-tight flexible tube, when moving, has negligible volume change during deformation thereof and the holding unit and the pipette body are spaced apart by a fixed distance.

2. The device according to claim 1, wherein:
the flexible tube has minimal expandability.

3. The device according to claim 2, comprising:
an intermediate piece, provided the holding unit, to which the fluid-tight flexible tube and, a replaceable pipette tip are attachable.

4. A pipette array comprising an array of devices according to claim 3, wherein:
the devices are disposed in a spatially fixed arrangement relative to one another, and
the array includes pipette tips which are borne together in the holding unit.

5. The pipette array according to claim 3, wherein:
pipette tips of the array of devices are linearly moveable in parallel.

6. The pipette array according to claim 3, wherein:
the pipette tips in an idle position are disposed in a plane.

7. A pipette array comprising an array of devices according to claim 2, wherein:
the devices are disposed in a spatially fixed arrangement relative to one another, and
the array includes pipette tips which are borne together in the holding unit.

8. The device according to claim 2, wherein:
the pipette tip is one-piece and is connected directly to the flexible tube.

9. The device according to claim 1, wherein:
the pipette tip is spring-tensioned in the holding unit and is movable relative to the holding device from an idle position by a force acting against the spring.

10. The device according to claim 9, comprising:
an intermediate piece, provided the holding unit, to which the fluid-tight flexible tube and, a replaceable pipette tip are attachable.

11. A pipette array comprising an array of devices according to claim 10, wherein:
the devices are disposed in a spatially fixed arrangement relative to one another, and
the array includes pipette tips which are borne together in the holding unit.

12. A pipette array comprising an array of devices according to claim 9, wherein:
the devices are disposed in a spatially fixed arrangement relative to one another, and
the array includes pipette tips which are borne together in the holding unit.

13. The device according to claim 9, wherein:
wherein the pipette tip is one-piece and is connected directly to the flexible tube.

14. The device according to claim 1, wherein:
the pipette tip is one-piece and is connected directly to the fluid-tight flexible tube.

15. The device according to claim 14, comprising:
an intermediate piece, provided the holding unit, to which the fluid-tight flexible tube and, a replaceable pipette tip are attachable.

16. A pipette array comprising an array of devices according to claim 15, wherein:
the devices are disposed in a spatially fixed arrangement relative to one another, and
the array includes pipette tips which are borne together in the holding unit.

17. A pipette array comprising an array of devices according to claim 14, wherein:

the devices are disposed in a spatially fixed arrangement relative to one another, and the array includes pipette tips which are borne together in the holding unit.

18. The device according to claim 1, comprising:

an intermediate piece, provided the holding unit, to which the fluid-tight flexible tube and, a replaceable pipette tip are attachable.

19. A pipette array comprising an array of devices according to claim 18, wherein:

the devices are disposed in a spatially fixed arrangement relative to one another, and the array includes pipette tips which are borne together in the holding unit.

20. A pipette array comprising an array of devices according to claim 1, wherein:

the devices are disposed in a spatially fixed arrangement relative to one another, and the array includes pipette tips which are borne together in the holding unit.

21. A pipette array comprising an array of devices according to claim 20, wherein:

the devices are disposed in a spatially fixed arrangement relative to one another, and the array includes pipette tips which are borne together in the holding unit.

22. The device according to claim 1, wherein:

the pipette tip is one-piece and is connected directly to the flexible tube.

23. The device according to claim 1, wherein:

an intermediate piece, provided the holding unit, to which the fluid-tight flexible tube and, a replaceable pipette tip are attachable.

* * * * *